United States Patent [19]
Hermentin et al.

[11] Patent Number: 6,096,555
[45] Date of Patent: Aug. 1, 2000

[54] PROCESS FOR CHARACTERIZING THE GLYCOSYLATION OF GLYCO-PROTEINS AND FOR THE IN VITRO DETERMINATION OF THE BIO-AVAILABILITY OF GLYCO-PROTEINS

[75] Inventors: Peter Hermentin; Reinhild Witzel, both of Marburg, Germany

[73] Assignee: Dade Behring Marburg GmbH, Marburg, Germany

[21] Appl. No.: 09/000,307

[22] PCT Filed: May 30, 1996

[86] PCT No.: PCT/EP96/02319

§ 371 Date: Jan. 26, 1998

§ 102(e) Date: Jan. 26, 1998

[87] PCT Pub. No.: WO97/05490

PCT Pub. Date: Feb. 13, 1997

[30]     Foreign Application Priority Data

Jul. 26, 1995 [DE]  Germany .......................... 195 27 054

[51] Int. Cl.[7] .................................................. G01N 33/68
[52] U.S. Cl. ................................ 436/87; 436/86; 436/161
[58] Field of Search ................................ 436/63, 86, 87, 436/161

[56]                References Cited

PUBLICATIONS

Aoyagi, "Carbohydrate–based Measurments on Alpha–fetaprotein in the Early Diagnosis of Heptocellular Carcinoma", GLYCO. J., 12(3):194–199 (Jun. 1995).

De Graaf et al., "Iflammation–induced Expresion of Sialyl Lewis X–containing Glycan Structures on $\alpha_1$–Acid Glycoprotein (Orosomucoid in Human Sera", J. Exp. Med., 177:657–666 (Mar. 993).

De Jong et al., "Transferrin Microheterogeneity as a Probe in Normal and Disease States", GLYCO. J., 12:219–266 (1995).

Hardy et al., "Monosaccharide Analysis of Glycoconjugates by Anion Exchange Chromotography with Pulsed Amperometric Detection", Analyt. Biochem., 170:54–62 (1988).

Hermentin et al., "The Mapping by High–pH Anion–Exchange Chromatography with Pulsed Amperometric Detection and Capilary Electrophoresis of the Carbohydrate Moieties of Human Plasma $\alpha$–Acid Glycoprotein[1,2]", Analyt. Biochem., 206:419–429 (1992).

Hermentin and Seidat, "Micro–Scale Analysis of N–Acetylneuraminic Acid", GBF Monographs, 15:185–188 (1991).

Hermentin et al., "A Strategy for the Mapping of N–Glycans by High–pH Anion–Exchange Chromatography with Pulsed Amperometric Detection[1,2]", Analyt. Biochem., 203:281–289 (1992).

Hermentin et al., "The Hypothetical N–Glycan Charge: A Number That Characterizes Protein Glycosylation", Glycobiology, 6(2) 217–230 (1996).

Hokke et al., "Structural Analysis of the Sialylated—and O–linked Carbohydrate Chains of Recombinant Human Erythropoietin Expresses in Chinese Hamster Ovary Cells", Structural Determination Of Glycoprotein Glycans (Doctoral Thesis) 4:51–90 (1993).

Koch, "Einführung in dies Biopharmazie", Österreichische Apotheker–Zeitung, 29:313–320 (Apr. 1975).

Lee and Rice, "Fractionation of Glycopeptides and Oligosaccharides from Glycoproteins by HPLC", Glycobiology—A Practical Approach, ch. 3C, pp. 127–163 (1994).

Mackiewicz and Mackiewicz, "Glycoforms of Serum $\alpha$1–Acid Glycoprotein as Markers of Inflammation and Cancer", GLYCO. J., 12:241–247 (1995).

Nimitz et al., "Structures of Sialylated Oligosaccharides of Human Erythropoietin Expressed in Recombinant BHK–21 Cells", Eur. J. Biochem., 213:39–56 (1993).

Nuck et al., "Optimized Deglycosylation Glycoproteins by Peptide–N$^4$—(N–acetyl–$\beta$–glucosaminy)– asparagine Amidase from *Flavobacterium meningosepticum*", GLYCO. J., 7:279–286 (1990).

Orntoft and Bech, "Circulating Blood Group Related Carbohydrate Antigens as Tumour Markers", GLYCO. J., 12:200–205 (1995).

Ritschel, "Graphic Approach to Clinical Pharmacokinetics", 1 ed., pp. 1–18 (1984).

Shahangian et al., "Plasma Protein–Bound Sialic Acid in Patients with Colorectal Polyps of Known Histology", Clin. Chem., 37(2):200–204 (1991).

Turner et al., "Glycosylation of Alpha–1–Proteinase Inhibitor and Haptoglobin in Ovarian Cancer; Evidnece for Two Differenct Mechanisms", GLYCO. J., 12:211–218 (1995).

Watson et al., "Structure Determination of the Intact Major Sialylated Oligosaccharide Chains of Recombinant Human Erythropoietin Expressed in Chinese Hamster Ovary Cells", Glycobiology, 4(2):227–237 (1994).

*Primary Examiner*—Maureen M. Wallenhorst
*Attorney, Agent, or Firm*—Finnegan, Henderson, Farabow, Garrett & Dunner, L.L.P.

[57]                ABSTRACT

The present invention involves a process for characterizing the glycosylation of glyco-proteins and an in vitro process for determining the bioavailability of glyco-proteins, based on the "hypothetical charge number" (or N) and usable for both endogenic and exogenic glyco-proteins.

15 Claims, 4 Drawing Sheets

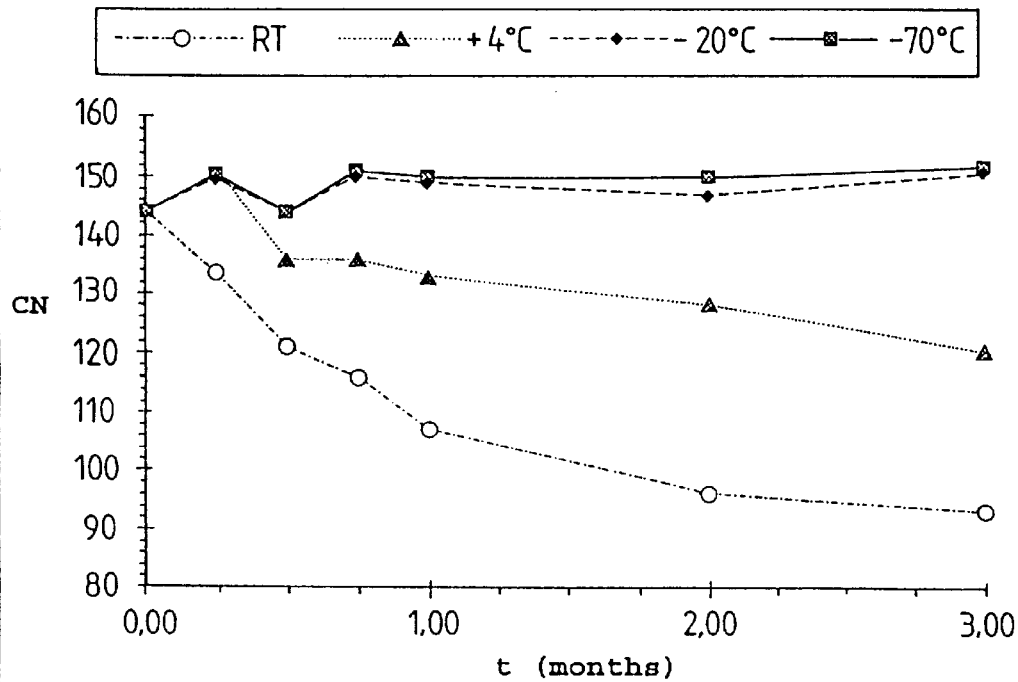
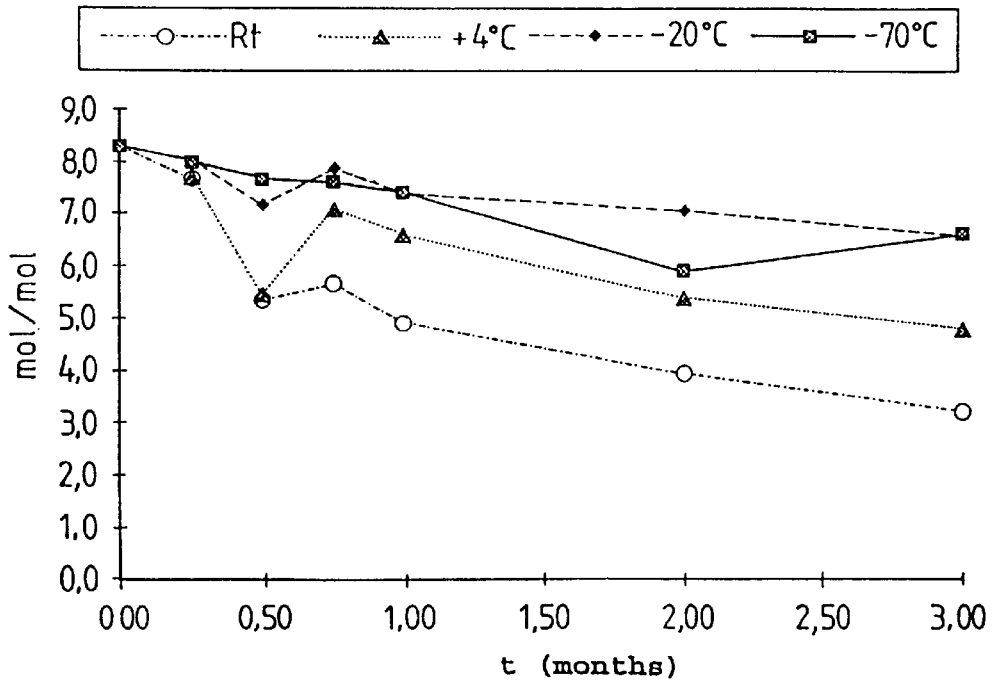

PROCESS FOR CHARACTERIZING THE GLYCOSYLATION OF GLYCO-PROTEINS AND FOR THE IN VITRO DETERMINATION OF THE BIO-AVAILABILITY OF GLYCO-PROTEINS

The present invention relates to a process for characterizing the glycosylation of glycoproteins and to an in-vitro process for determining the bioavailability of glycoproteins, which process is based on the "hypothetical charge number" (termed "N" below) and can be employed both for endogenous glycoproteins and exogenous glycoproteins.

In this connection, exogenous glycoproteins are, for example, recombinant therapeutic glycoproteins (such as interleukin 2, erythropoietin, tissue plasminogen activator or antithrombin III) which are obtained from mammalian cells. In recent years, these substances have aroused substantial interest in scientific, pharmaceutical and official institutions.

In this connection, endogenous glycoproteins are human or non-human (e.g. bovine) serum glycoproteins (such as human $\alpha_1$-acid glycoprotein, human transferrin or bovine fetuin, and also glycoproteins of other species such as chicken ovomucoid or porcine thyroglobulin).

The investigation, development and production of therapeutic glycoproteins, and their official and/or clinical licensing, requires elaborate analysis with regard to in-vivo half life, biological safety, product definition and batch consistency.

In this respect, the proportion of sialic acid (N-acetylneuraminic acid, Neu5Ac), in particular, has previously been an important parameter since it is assumed that the presence or absence of Neu5Ac has a decisive influence on the circulating half life of a glycoprotein in the blood and on its clearance. However, precise investigation of the carbohydrate side chains of a glycoprotein demands very elaborate and complex analysis which requires a high degree of expertise and a wide range of equipment (for example GC-MS, FAB-MS and high-resolution 1H NMR spectroscopy).

In particular, the authorities which are responsible for licensing therapeutic glycoproteins (e.g. EPO) still require, for safety reasons, the very elaborate, time-consuming, expensive but relatively inexact determination of the therapeutic activity of the glycoprotein in animal experiments (in-vivo assay). More advantageously, however, an in-vitro assay should be available which, firstly, can be carried out in a simple and reliable manner and, secondly, meets the justifiably high demands of the licensing authorities.

With regard to implementing additional determinations, some success has already been achieved in replacing the tedious and expensive methods of glycoanalysis with standardizable chromatographic methods (Hermentin et al. (1992) *Anal. Biochem.* 203, 281–289; idem., ibid., (1992) 206, 419–429). However, there has not previously been any parameter which would have satisfied the requirements of the licensing authorities as a replacement for an in-vivo assay for the bioavailability of a glycoprotein.

The present invention was therefore based on the technical problem of providing an in-vitro process which is suitable for determining the degree of glycosylation of a glycoprotein in such a simple and reliable manner that the process is suitable for replacing the known in-vivo processes, for example for determining bioavailability and batch consistency.

This technical problem is solved by providing the embodiments which are characterized in the patent claims.

It has been ascertained, surprisingly, that N correlates outstandingly well, and with good reproducibility, with the bioavailability/biological activity of a glycoprotein as found in in-vivo methods. Because of the good reproducibility and the analytical accuracy, N can advantageously also be employed in a process for determining batch consistency.

The present investigations allow the conclusion that N characterizes the "glycosylation status". Glycosylation can therefore be compared in a simple manner by determining N.

In connection with the present invention, the "glycosylation status" of a glycoprotein is understood as being the composition of the glycan pool comprising bi-, tri- and tetra-antennary glycans and their respective degree of sialylation (the content of bound N-acetylneuraminic acid) and the content of sulfate or phosphate groups.

The bioavailability of a glycoprotein therapeutic agent is understood as being the ability of the therapeutic agent to display its biological and/or therapeutic activity in vivo. Accordingly, the bioavailability and the biological activity are determined in a crucial manner by the in-vivo clearance behavior, that is the removal of the therapeutic agent from the blood circulation. For example, it is known that when EPO lacks the N-acetylneuraminic acid which is bound terminally in the N-glycosidic sugar chains, it is removed from the blood circulation very rapidly in the liver by way of the so-called "asialo receptor" and is consequently unable to display its biological activity.

Surprisingly, the N of a therapeutic glycoprotein correlates with the in-vivo half life of the glycoprotein and consequently constitutes a completely novel measurement parameter which makes it possible to assess in advance, and in a very simple manner, the clearance behavior which is to be expected from each batch of the therapeutic glycoprotein. As a consequence, N also makes it possible to draw conclusions with regard to the biological safety and the therapeutic activity to be expected for each batch of the glycoprotein. Therefore, when the N of each batch of a therapeutic glycoprotein is determined, the very elaborate, time-consuming, expensive and relatively inexact determination of the therapeutic activity of the glycoprotein in animal experiments (in-vivo assay) can, for example, be dispensed with. This additionally enables a new and substantial contribution to be made to reducing animal experiments and consequently to improving animal welfare. At the same time, N constitutes a particularly suitable measure of batch consistency.

The fact is also surprising, and of particular value, that, in the case of endogenous glycoproteins, that is, for example, in the ease of a human serum glycoprotein in which the glycosylation varies, for instance, with a disease, N can be defined as a diagnostic measurement parameter which correlates with the disease and which consequently makes it possible to draw conclusions about the severity of the disease. In inflammatory diseases, for instance, this applies, for example, to the "acute phase glycoproteins", such as $\alpha_1$-acid glycoprotein, whose glycosylation is known to alter when an inflammation develops (De Graaf et al. (1993) *J. Exp. Med.* 177, 657–666). This is also the case in tumor diseases, in which the content of protein-bound sialic acid (and consequently the glycosylation) changes as the tumor disease progresses (Shahangian et al. (1991) *Clin. Chem.* 37, 200–204).

For example, determining the N of a tumor-associated glycoprotein from a tumor patient makes it possible to draw conclusions about the stage of the tumor disease, based on the observation that the sialylation changes during the growth of the tumor (Shahangian et al., ibid., p. 200).

Recently, a series of articles providing evidence that the glycosylation of particular glycoproteins changes with a disease were published in a special volume of Glycokonjugate J. (Volume 12, No. 3, June 1995). Thus, for example:

α-fetoprotein is suitable for the early diagnosis of hepatocarcinoma (Aoyagi, ibid., p. 194–199), circulating blood group-related carbohydrate antigens are suitable for use as tumor markers (Ørntoft and Bech, ibid., p. 200–205), $\alpha_1$-proteinase inhibitor and haptoglobin are suitable for diagnosing ovarian carcinoma (Turner et al., ibid., p. 211–218), transferrin is suitable for characterizing cerebrospinal fluid and for diagnosing clandestine alcohol abuse and the carbohydrate-deficient glycoprotein syndrome (De Jong et al., ibid., p. 219–226) and glycoforms of $\alpha_1$-acid glycoprotein are suitable for diagnosing inflammations and cancer (Mackiewicz & Mackiewicz, ibid., p. 241–247).

In all these, and other, diagnoses, N can advantageously be enlisted for determining the stage of a disease in a patient.

Of importance for the invention is the realization that the distribution of the charge-uniform glycan groups, in particular those exhibiting differing degrees of sialylation (asialo to pentasialo), is a crucial index of the bioavailability of a glycoprotein and of its batch consistency. In this context, it is of importance to the invention that the charge-uniform glycan groups are weighted in accordance with their charge, in particular their degree of sialysation. These weighted fractions are combined in the N.

The N of a glycoprotein can be determined very easily and accurately, for example by using an optimized and standardized chromatographic method, as has recently been described (Hermentin et al. (1992) *Anal. Biochem.*, 203, 281–289).

The N of a glycoprotain is determined by a) liberating the glycan pool of the glycoprotein in a manner known per se, either chemically for example (by means of hydrazinolysis) or enzymically (for example using PNGase F) and then isolating it, b) fractionating the pool, primarily according to charge, by means of ion exchange chromatography (preferably using HPAE-PAD) in a manner known per se, c) determining, in a manner known per se, the percentage fractions represented by the areas of the peak or glycan groups which have been separated according to charge, d) multiplying the percentage fractions represented by the areas of the peak or glycan groups in the neutral (asialo, as), monosialo (MS), disialo (DiS), trisialo (TriS), tetrasialo (TetraS) and pentasialo (PentaS) ranges by zero (asialo), 1 (MS), 2 (DiS), 3 (TriS), 4 (TetraS) and 5 (PentaS), respectively, and e) summing over the products which are obtained in each case.

For the purpose of determining N, the Asn-linked sugar chains of the glycoproteins can, in a manner known per se, be liberated in principle in two ways—namely either chemically (for example by means of hydrazinolysis) or enzymically (for example using N-glycanase or PNGase F). The enzymic method requires reaction conditions which have to be optimized in each case—for example carrying out a preliminary tryptic digestion of the glycoprotein or adding a suitable detergent. The hydrazinolysis also requires special know-how if the side reactions are to be minimized. However it can nowadays be carried out in a fully automated manner using the instrument supplied by Oxford GlycoSystems (the GlycoPrep 1000).

The EPAEC fractionates the N-glycans primarily according to charge, i.e. according to the number of sialic acid residues they possess (Hermentin et al. (1992) *Anal. Biochem.* 203, 281–289), which is why it is especially suitable for determining the N-of glycoproteins.

Thus, it was found that when HPAE-PAD is used to map the N-glycan pools of glycoproteins, glycans of the same charge—as a rule glycans having the same number of Neu5Ac residues—can in the main be brought together in clearly separate peak groups. This is exemplified by the glycan pool of rhu IL-4R (CHO) (FIG. 1). In this context, a proven approach is to use two internal standards, one of which (S1=e.g. LNnT or LNFP-V, Oxford GlycoSystems) elutes before the individual peaks of the glycan pool while the other [S2=(Neu5Ac)3] elutes after the individual peaks of the glycan pool, such that the detected glycans are always located in the RT region between the two standards and their total peak area, corresponding to 100%, can readily be ascertained using the chromatographic analytical software. Thus, the total peak area is obtained by integrating and summing the peaks which are located between the retention times of the two standards, S1 and S2. In the same way, the peak groups having 0, 1, 2, 3, 4 and 5 negative charges, which groups have been separated according to charge, can also be combined by integration and their respective peak group areas, "A", can be calculated as percentage fractions of the total peak area of the glycan pool. In making this calculation, it is assumed that all the glycans have the same response factor.

The hypothetical charge number N is calculated in accordance with equation I:

$$N = A_{(as)}*0 + A_{(MS)}*1 + A_{(DiS)}*2 + A_{(TriS)}*3 + A_{(TetraS)}*4 + A_{(PentaS)}*5 \quad (I)$$

where $A_{(as)}$, $A_{(MS)}$, $A_{(DiS)}$, $A_{(TriS)}$, $A_{(TetraS)}$ and $A_{(PentaS)}$ are the respective percentage peak group area fractions in the asialo, monosialo, disialo, trisialo, tetrasialo and pentasialo ranges, based on the peak areas=100%.

In this way, an N of about 400 is obtained for a glycoprotein, such as recombinant erythropoietin, which predominantly possesses tetra-antennary tetrasialo (C4-4*) structures. In an analogous manner, an N of about 300 is obtained for a glycoprotein, such as bovine fetuin, which predominantly possesses triantennary trisialo (C3-3*) structures, and an N of about 200 for a glycoprotein, such as human antithrombin III, which predominantly possesses biantennary disialo (C2-2*) structures. An N of about 0 is obtained for a glycoprotein, such as bovine pancreatic ribonuclease B, which only possesses asialo structures, for example, or for a glycoprotein, such as chicken ovomucoid, which possesses so-called truncated forms.

From the analytical point of view, it is desirable to first of all fractionate the glycan pool which has been isolated from a glycoprotein chromatographically in accordance with the degree of sialylation before making use of other separating methods as required. This chromatographic separation can be carried out using anion exchange columns, such as Glycopac™ DEAE (Waters), Mono Q™ (Pharmacia) or Gen-Pak™ FAX (Waters), or using HPAEC (high-pH anion exchange chromatography) on pellicular anion exchange resins (CarboPak PA-1™ or CarboPak PA-100™, Dionex) (Lee and Rice (1994) in: "Glycobiology—A Practical Approach", Chapter 3C, pp. 127–163, IRL Press, Editors: Fukuda and Kobata).

It was recently demonstrated that high-pH anion exchange chromatography with pulsed amperometric detection (HPAE-PAD) is extremely satisfactory in meeting the criteria for a rapid, economical and, in particular, readily reproducible chromatographic method for structurally classifying the oligosaccharide chains of glycoproteins (Hermentin et al. (1992) *Anal. Biochem.* 203, 281–289; Hermentin et (1992) Anal. Biochem. 206, 419–429). In this method, the oligosaccharides are separated on an anion exchange column (CarboPac PA-1 or CarboPac PA-100 from Dionex) under alkaline conditions. This method initially separates the N-glycans which have been isolated from the glycoprotein according to their charge, thereby providing information on the composition of the N-glycan pool composed of neutral (asialo) structures and mono-, di-, tri- and tetra-sialo structures (that is N-glycans possessing from zero to four negatively charged neuraminic acid residues). The sugars are measured very selectively and sensitively, and without derivatizing the glycans, by means of pulsed amperometric detection at a gold electrode.

The determination of N was validated, by way of example, in a large number of experiments using rhu IL-4R (a therapeutic glycoprotein supplied by Behringwerke AG). These experiments were able to demonstrate that the hypothetical charge number may be regarded as being a novel, informative, reliable and characteristic parameter of protein glycosylation.

Various examples of determining N from the resulting HPAE-PAD chromatograms are given below. For this, the glycans were liberated from a variety of glycoproteins, in a manner known per se, either by means of automated hydrazinolysis (using the Oxford GlycoSystems, OGS, GlycoPrep 1000™) or enzymically (using PNGase F), and then isolated, or else purchased directly, as glycan pools, from Oxford GlycoSystems and measured by means of HPAE-PAD in a standard "S" gradient (Hermentin et al. (1992) Anal. Blochem. 203, 281–289).

The determination of N is demonstrated, by way of example, using the HPAE-PAD chromatogram of rhu IL-4R as an example (FIG. 1); the relevant calculation is to be found in Table 1. N was determined in an analogous manner in all the other examples.

The determination of N for $\alpha_1$-acid glycoprotein (AGP) diverges somewhat from the determinations for the other glycoproteins mentioned since AGP possesses antennary fucose residues in its N glycans (Hermentin et al. (1992) Anal. Biochem. 206, 419–429). In HPAEC, N glycans of this latter type elute approximately 4 min earlier in the standard "S" gradient as compared with the corresponding non-fucosylated N-glycan. For this reason, the clean separation into charge-uniform peak groups which is observed in the other examples is not obtained in the case of the AGP N-glycan pool; instead, these peak groups become superposed (Hermentin et al. (1992) (Anal. Biochem. 206, 419–429). In the case of AGP, the hypothetical charge number was determined using the charge-based peak assignment described by Hermentin et al. (1992) (Anal. Biochem. 206, 419–429). This method was used to determine N in Examples 9 and 10.

In those cases in which the N-glycans of a glycoprotein contain sulfate groups, for example, in addition to neuraminic acid, the N value is determined, for example, by multiplying the peak groups which have been separated according to charge and which are located in the 6- or 7-charge region of the chromatogram by 6 or 7, respectively.

The N values determined for a number of glycoproteins are listed together in Table 3.

Note:

S1: Internal Standard 1

S2: Internal Standard 2

In the chromatogram, the glycans are located between S1 and S2. The peaks prior to S1 are derived from the hydrazinolysis; the nature of the peaks after S2 is unknown.

FIG. 2

Figure 2:
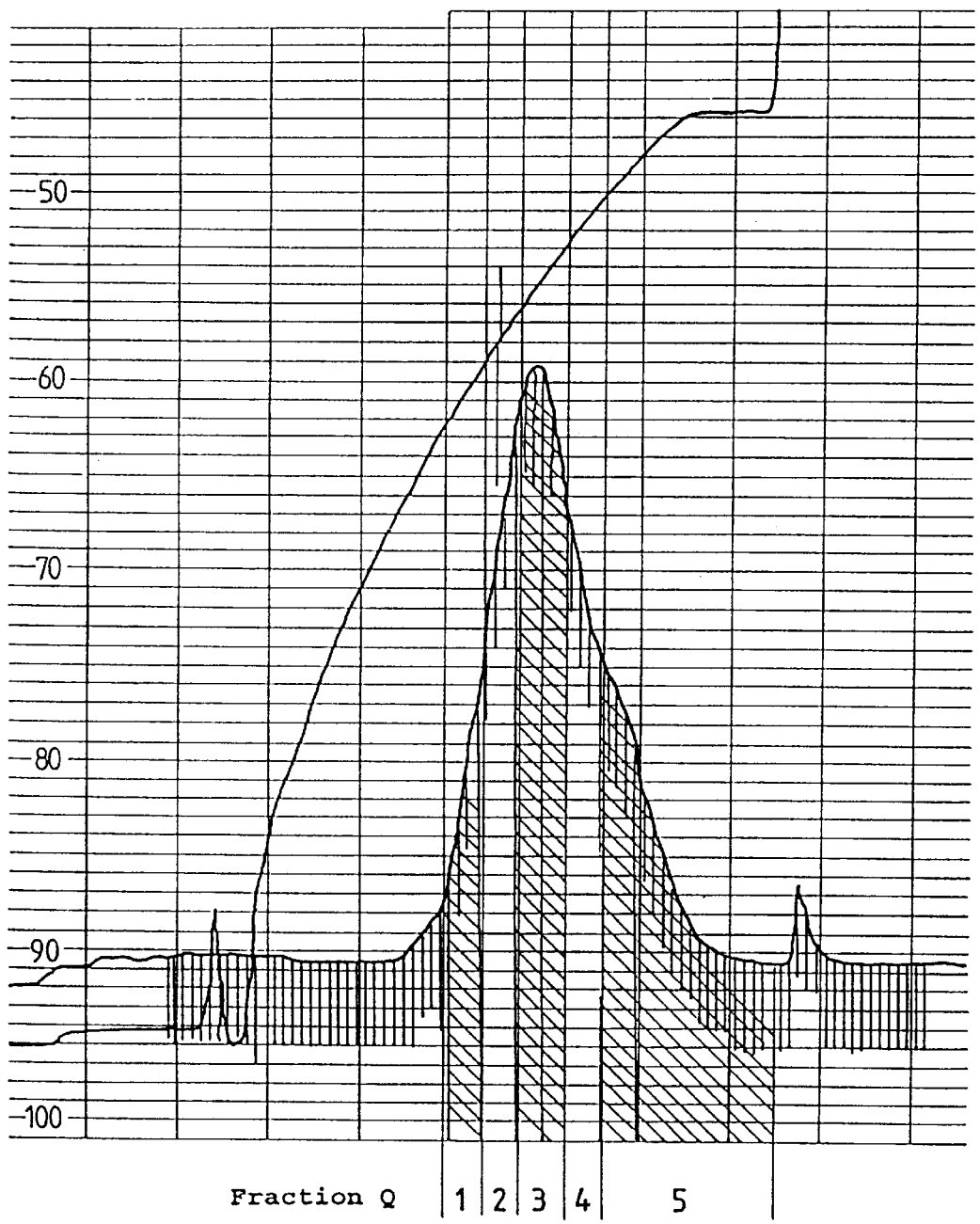

FIG. 2 shows the fractionation of rhur IL-4R (batch 018PP) by means of anion exchange chromatography on Q Sepharose FF.

FIG. 3

Figure 3:
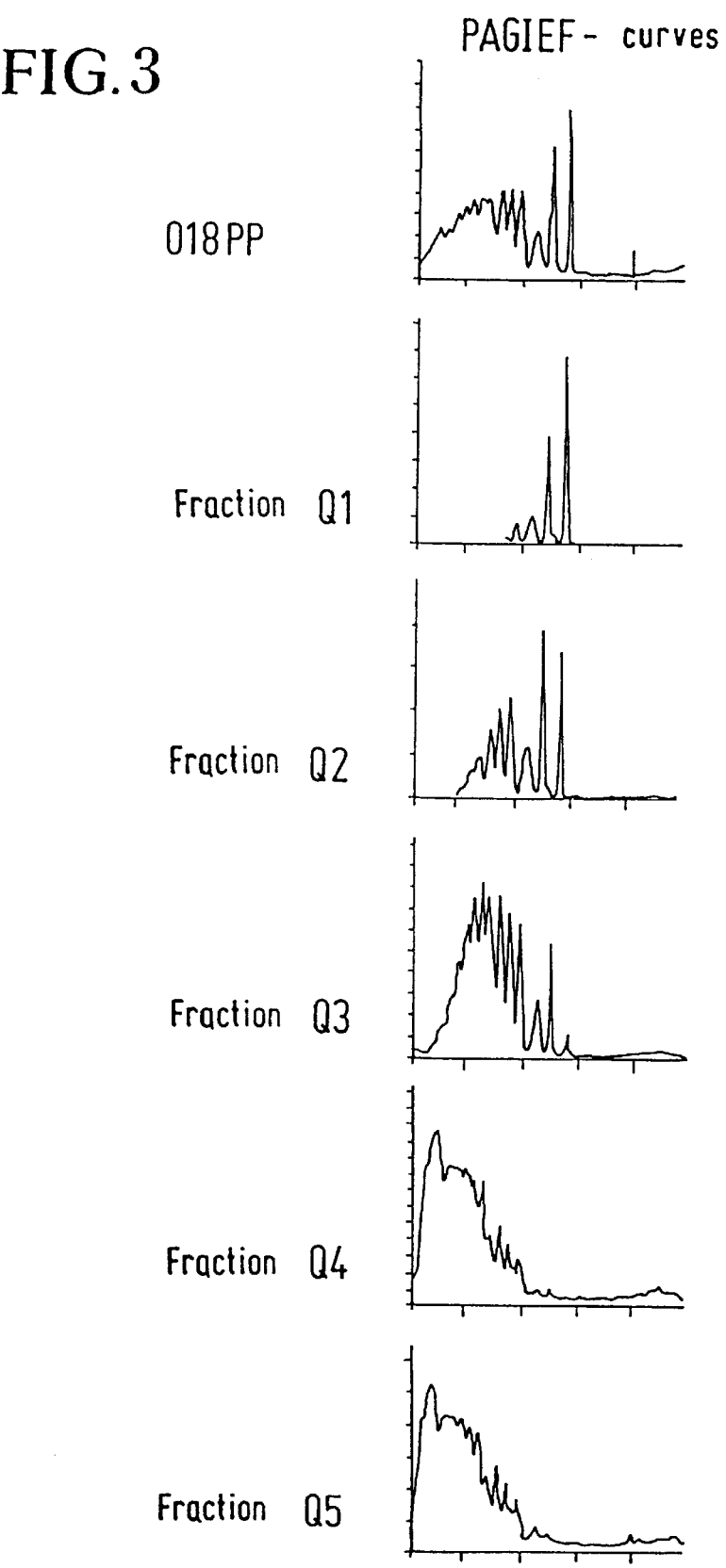

FIG. 3 shows the isoelectric focussing (IEF) of the Q Sepharose fractions of rmur IL-4R batch 018PP which were obtained as shown in FIG. 2.

The associated analytical data are contained in Table 3.

FIG. 4

FIG. 4a shows the decline in the n, and FIG. 4b shows the decline in the nana content of rhu IL-4R in the culture supernatant during storage at room temperature (RT), +4° C., −20° C. and −70° C.

The examples described below do not limit the invention.

EXAMPLE 1

Validation of the Determination of N Using rhu IL-4R (CEO) (batch E4-930914)

a) Validation using 1.0 mg of rhu IL-4R per hydrazinolysis reactor

The determination of N was validated using rhu IL-4R (CHO) as a reference glycoprotein. For this, the glycan pool of the IL-4R sample (batch E4-930914, Behringwerke AG) was liberated, and then isolated, on 3 different days in 6 different mixtures by means of automated hydrazinolysis in the presence of LNFP-V as the internal S1 standard (GlycoPrep 1000™, Oxford GlycoSystems; simultaneous hydrazinolysis in both reactors; 1 mg of IL-4R added per reactor). Each of the 6 glycan pools was desalted through Sephadex G-25 superfine (Pharmacia) (column packing, 21×1 cm) and measured three times (on three different days; adding S2=(Neu5Ac)3 on each occasion) in the EPAE-PAD; N was then determined in each case from each of the resulting chromatograms using equation 1. Table 1 gives a detailed listing of the peak area fractions which were in each case integrated for each of the 18 HPAE-PAD single runs and of the summations which were in each case carried out in accordance with equation 1. The HPAE-PAD mapping chromatogram shown in FIG. 1 serves as an illustrative example and as a reference run.

In these experiments, the N of the said IL-4R sample was determined, with a very high degree of reproducibility, to be N=201±3 (CV=1.4%) (Table 2).

b) Validation using 0.50 mg of rhu IL-4R per hydrazinolysis reactor

In a second validation experiment, the hydrazinolysis was carried out in 6 different mixtures in an analogous manner to Example 1a) using 0.5 mg of rhu IL-4R per reactor, and the results were averaged. In this case, the N was found to be N=194±5 (CV=2.3%) (Table 2).

TABLE 1

Figure 1:
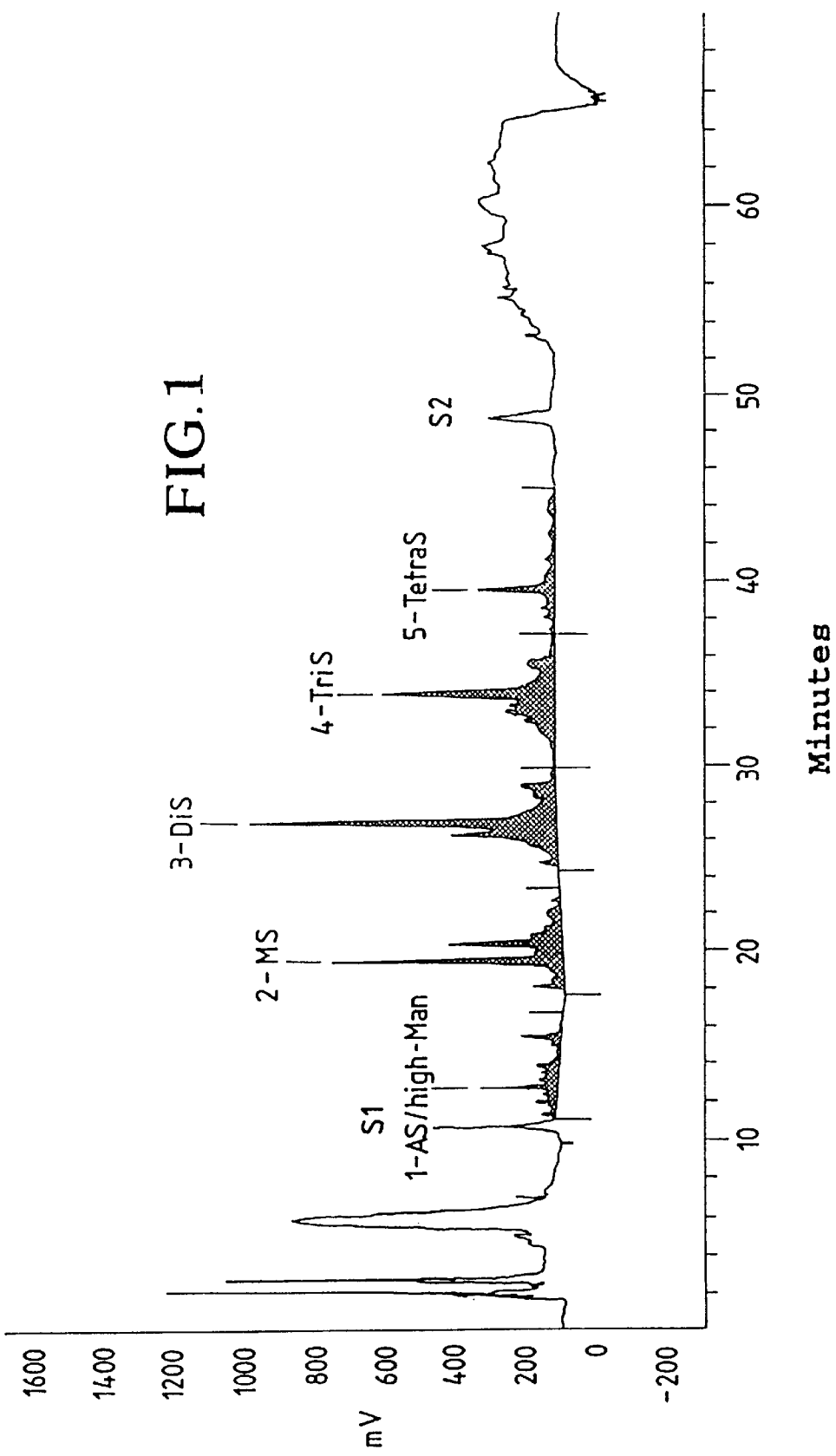
FIG. 1 shows the N-glycan mapping profile of rhu IL-4R (batch E4-930914) following separation by means of HPAE-PAD under standard conditions as described by Hermentin et al., Anal. Biochem. 203 (1992), pp. 281–289.

Calculating the N value of the mapping profile of rhu IL-4R (CHO) (batch E4-9300914) shown in FIG. 1

| File No. | Peak Group No. | Retention time of the highest peak (min) | Integration range (peak group) | Percentage fraction of the peak group area (%) | Multi-plier | Charge number constituent |
|---|---|---|---|---|---|---|
| 0940964K.D42 | 1 | 12.57 | asialo/high mannose | 9.70 | 0 | 0 |
| | 2 | 19.23 | monosialo (MS) | 23.31 | 1 | 23.31 |
| | 3 | 29.69 | disialo (DiS) | 31.81 | 2 | 63.62 |
| | 4 | 33.73 | trisialo (TriS) | 25.38 | 3 | 76.14 |
| | 5 | 39.44 | tetrasialo (TetraS) | 9.81 | 4 | 39.24 |
| | | | Total peak area | 100.01 | | Charge number 202 |

EXAMPLE 2
Determination of the N Value of rhu IL-4R (CHO) (Batch E4-930914) Following Digestion with PNGase F—With and Without CHAPS The N-glycans were liberated after reducing the glycoprotein (500 µg) with dithioerythrol (DTE; 25 µl of an 0.3 M aqueous solution of DTE) at 70° C. for 10 min. The excess of DTE was removed by concentrating in a Centricon cartridge having an exclusion limit of 10,000 D (from Amicon), and the concentrate was then washed three times in the Centricon tube with glycanase digestion buffer. The concentrate was then transferred to an Eppendorf capsule and digested with PNGase F (Boehringer Mannheim; 5 units) in glycanase digestion buffer (500 µl) in 50 mM of sodium phosphate buffer, pH 7.6, at 37° C. for 48 h, a) in the presence and b) in the absence of 0.5% CHAPS.

The following N values were determined after desalting in analogy with Example 1a:
a) (without CHAPS): N=208;
b) (with CHAPS); N=206 (Table 2).

This experiment therefore demonstrated that it is not possible to achieve any improvement in deglycosylation by adding the detergent CHAPS.

c) As an alternative, rhu IL-4R was carboxamidomethylated after having been reduced with dithiothreitol (DDT) and then digested with trypsin, as described in Hermentin et al. (*Anal. Biochem.* (1992), 206, 419).

After that, the glycan liberation took place in the presence of 0.5% CHAPS in analogy with Example 2b). In this case, the N value was found to be N=200 (Table 2).

d) The rhu IL-4R was digested in analogy with Example 2c) using the enzyme Lys C instead of the enzyme trypsin.

Otherwise, the procedure was as for Example 2c). In this case, the N value was found to be N=204 (Table 2).

The mean of the charge numbers determined in accordance with Examples 2a)–2d) is N=204.5±3.4 (CV=1.7%) (Table 2).

These four charge numbers are in good agreement with the mean charge numbers of N = 201 (1a; 1.0 mg of IL-4R per reactor) and N =194 (1b; 0.5 mg of IL-4R per reactor) which were determined in Example 1a and 1b following automated hydrazinolysis. (Table 2).

TABLE 2

Validation of the determination of N using rhu IL-4R (CHO) as a model glycoprotein

| Batch | Preparation of the glycan pool | N Individual determination | N Mean value | Standard deviation | CV | Number of experiments | Number of HPAE-PAD runs | Exp. |
|---|---|---|---|---|---|---|---|---|
| E4-930914 | GlycoPrep (1.0 mg/reactor) | | 201 | +/− 3 | 1.4% | 6 | 18 | 1a |
| E4-930914 | GlycoPrep (0.5 mg/reactor) | | 194 | +/− 5 | 2.3% | 6 | 18 | 1b |
| E4-930914 | PNGase F (without CHAPS) | 208 | | | | | | 2a |
| E4-930914 | PNGase F (with 0.5% CHAPS) | 206 | | | | | | 2b |
| E4-930914 | PNGase F (trypsin/with 0.5% CHAPS) | 200 | 204.5 | +/− 3.4 | 1.7% | 4 | 4 | 2c |
| E4-930914 | PNGase F (Lys C/with 0.5% CHAPS) | 204 | | | | | | 2d |
| B11-930406 | GlycoPrep (0.5 mg/reactor) | | 243 | | | | | 3 |
| B11-930406 | PNGase F (without CHAPS) | 241 | | | | | | 4a |
| B11-930406 | PNGase F (with 0.5% CHAPS) | 246 | 243.5 | +/− 3.5 | 1.5% | 2 | 2 | 4b |

EXAMPLE 3
Determination of the N Value of rhu IL-4R (CHO) (Batch B11-930406) Following Automated Hydrazinolysis The hydrazinolysis was carried out in analogy with Example 1b using 0.5 mg of rhu IL-4R. The N value was found to be N=243.

EXAMPLE 4
Determination of the N Value of rhu IL-4R (CHO) (batch B11-930406) Following Digestion With PNGase F—Without and With CHAPS The N-glycans were liberated in analogy with Examples 2a) and 2b), respectively.

The following N values were found: a) (without CHAPS) N=241;

b) (with 0.5% CHAPS) N=246; mean value, N=243.5±3.5 (1.5%) (Table 2).

These two N values are in good agreement with the charge number of N=243 which was determined in Example 3a following hydrazinolysis, so that batch B11-930406 of rhu IL-4R can be stated to have an N value of N=243 (Table 2).

It was found, therefore, that, for the same culturing, harvesting and purification conditions, the material from clone B11-930406 (N=243) (Examples 3 and 4) contained a greater proportion of more highly charged and/or more highly antennary glycans than did the material from clone E4-930914 (N=204.5) (Examples 1 and 2).

EXAMPLE 5
A Comparison of N With Glycoanalytical Parameters Which are Known Per Se and With the In-Vivo Clearance Behavior of a Glycoprotein in the Mouse Model A preparation of soluble murine interleukin 4 receptor (rmur IL-4R, Behringwerke AG) which was isolated from BEK cells was fractionated, in a manner known per se, into 5 fractions, Q1–Q5, by passing it through an anion exchange resin (Q-Sepharose, Pharmacia) (FIG. 2). The individual fractions were analyzed (isoelectric focussing, sialic acid determination and content of monosaccharide components) in a manner known per se. The IEF band pattern was scanned, in a manner known per se, using gel analysis software. The resulting band scans are depicted in FIG. 3. The analytical data, which were obtained in a manner known per se, are shown in Table 3.

The content of N-acetylneuraminic acid (Neu5Ac; sialic acid) was determined as described by Hermentin and Seidat (in: *GBF Monographs,* Vol. 15, pp. 185–188, H. S. Conradt, ed., VCH, Weinheim/New York/Cambridge)

The monosaccharide determination was carried out in a manner known per se, as described by Hardy et al. (*Anal. Biochem.* (1988) 170, 54–62). The Neu5Ac/Gal (mol/mol) quotient was determined from the result of the monosaccharide analysis.

Note

Since, in normal N-glycans, Neu5Ac is always bonded to antennary galactose residues, the Neu5Ac/Gal (mol/mol) quotient makes it possible to calculate the content of terminal galactose. The terminal galactose of the N-glycans in turn exerts an influence on the clearance behavior of a glycoprotein since glycoproteins having a terminal galactose in the N-glycans are eliminated from the blood by way of the so-called asialo receptor in the liver. The degree of sialylation (Neu5Ac/Gal; mol/mol) consequently makes it possible to draw conclusions about the extent to which a glycoprotein can be expected to be cleared in the liver. However, the determination of the degree of sialylation turns out to be relatively inaccurate since the variances of the two tests (the Neu5Ac and Gal determinations) are summed in the degree of sialylation. For this reason, there is a requirement for a more accurate parameter which describes the clearance behavior of a glycoprotein in association with in-vivo administration.

The quotient of the molar proportion of mannose and galactose (Man/Gal; mol/mol), which provides an indication of the extent to which the N-glycans are composed of high-mannose structures and complex-type structures, was also ascertained from the result of the monosaccharide analysis.

Note

The Man/Gal ratio also makes it possible to draw conclusions about the clearance behavior which a glycoprotein can be expected to exhibit since glycoproteins containing high-mannose structures are also removed from the blood circulation by way of a receptor in the liver (the so-called high-mannose receptor). Since the content of high-mannose structures is also included in the calculation of the hypothetical charge number in accordance with equation 1, N also reflects the content of high-Man structures and consequently also makes it possible to predict the degree of clearance by way of the high-Man receptor.

The N values for the individual fractions were determined in analogy with Example 1.

TABLE 3

|  | Neu5Ac (µg/mg) | NeuAc/Ga (mol/mol) | Man/Gal (mol/mol) | AUD (µg/ml*min) | CL (ml/min) | N |
|---|---|---|---|---|---|---|
| Starting material: | 78.5 | 0.54 | 1.28 | 42.7 | 0.23 | n.b. |
| Fraction Q1 | 13.6 | 0.20 | 3.02 | 0.8 | 10.0 | 147 |
| Fraction Q2 | 38.2 | 0.42 | 1.99 | 5.3 | 2.00 | 191 |
| Fraction Q3 | 82.9 | 0.62 | 1.24 | 33.6 | 0.29 | 238 |
| Fraction Q4 | 109.5 | 0.67 | 1.04 | 63.7 | 0.16 | 248 |
| Fraction Q5 | 108.6 | 0.63 | 0.98 | 85.9 | 0.12 | 247 |

The clearance behavior of the individual fractions was also checked, in a manner known per se, in the mouse model (AUD) (Table 3).

For this, aliquots of the individual fractions were injected into mice and the clearance of the rmur IL-4R from the blood of the mice was monitored by ELISA.

The rate of IL-4R clearance was determined as follows:

Female BALB/C mice were given a bolus injection of IL-4R (10 µg 0.2 µg/kg) into the tail vein. At 5, 10 and 30 min after administration, blood samples for serum isolation were withdrawn by puncture from the retroorbital venous complex. The IL-4R concentration in the respective serum sample was determined by carrying out an ELISA. The curve of the IL-4R concentration which was determined in the serum plotted against time ($AUD_{5-30}$) was calculated using the so-called trapeze rule (Koch (1985), *Apoth. Ztg.,* 29, issue 17, April 1975). This curve was used to calculate the initial clearance ($Cl_{5-30}$) in accordance with the equation $Cl_{5-30} = dose/AUD_{5-30}$).

Result

As can be seen from the scans of the IEF bands shown in FIG. 3, fractions Q1 to Q4 exhibit continuous differences in their IEF glycoform banding patterns, whereas fractions Q4 and Q5 are found to be indistinguishable by IEF. However, isoelectric focussing suffers from the disadvantage that it cannot be assessed quantitatively, or can only be assessed quantitatively with very great difficulty, and therefore primarily yields a qualitative measurement parameter.

While the sialic acid content increases continuously from fraction Q1 (13.6 µg/mg) to fraction Q4 (109.5 µg/mg), it is found to be practically identical in fractions Q4 and Q5 (Table 3). The results of the sialic determination therefore correlate well with the results of the isoelectric focussing.

In a similar manner to the sialic acid content, but to a less marked extent, the degree of sialylation (Neu5Ac/Gal quotient) also increases from fraction Q1 (0.20 Neu5Ac residues per galactose residue) to fraction Q4 (0.67 Neu5Ac residues per galactose residue), but then falls off once again in fraction Q5 (0.63 Neu5Ac residues per galactose residue) to about the value of fraction Q3 (0.62 Neu5Ac residues per galactose residue) (Table 3). This fall in the analytical value of fraction Q5 to the value of fraction Q3 was not observed either in the sialic acid determination or in the isoelectric focussing. It has to be assumed, therefore, that the degree of sialylation (Neu5Ac/Gal; mol/mol) is a parameter which is less reliable than the Neu5Ac determination or the isoelectric focussing because the inaccuracies of the two individual tests (that is of the neuraminic acid determination and the monosaccharide component analysis) are summed in the sialylation degree quotient.

Conversely, the Man/Gal quotient decreases continuously from fraction Q1 (3.02 mol/mol) to fraction Q4 (1.04 mol/mol) and remains virtually constant within the limits of measurement accuracy in fraction Q5 (0.98 mol/mol) (Table 3). Because of its continuous progress from fraction Q1 to fraction Q5, the Man/Gal quotient also appears to be a reliable and meaningful parameter—in a similar way to the Neu5Ac determination and the isoelectric focussing.

As to be expected, N, as determined in accordance with equation 1 and/or Example 1, increases in parallel with the sialic acid content and progresses continuously from N=147 (fraction Q1) to N=248 (fraction Q4), whereas it remains constant from fraction Q4 (N=248) to fraction Q5 (N=247) (Table 3). Consequently, the determination of N which reflects both the results of the sialic acid determination and the qualitative course of isoelectric focussing very well and appears to be superior (like the Neu5Ac determination and IEF) to determining the degree of sialylation (Neu5Ac/Gal; mol/mol). (Example 6 below demonstrates that determining N is also superior to determining Neu5Ac).

The clearance behavior (AUD, area under data; $\mu$g/ml*min) of fractions Q1–Q5 was also determined in a manner known per se. In this connection, the circulation half life of IL-4R in mouse blood increases as the AUD increases. As can be seen from Table 3, the AUD increases continuously from fraction Q1 (AUD=1) to fraction Q5 (AUD=86). The AUD therefore correlates well with the IEF, the sialic acid content, the Man/Gal (mol/mol) quotient and the N for fractions Q1–Q4. The AUD is only found to diverge from the said measurement parameters in the case of fraction Q5. Thus, it was found that the clearance correlates closely with the charge number and that N—as compared with a suitable standard—enables satisfactory conclusions to be drawn with regard to the clearance behavior which a glycoprotein can be expected to exhibit in association with in-vivo administration.

Note

Because of a lack of material, it was not possible to determine, by repetition, whether this divergence of AUD from the remaining measured analytical values was a true reflection of the facts or was an artifact (outlier). In addition, the fact has to be noted that, for animal welfare reasons, the AUD was determined using only one mouse per AUD measurement point, thereby limiting the reliability of the AUD value as compared with the measured analytical values.

Result

Consequently, for the purposes of predicting the clearance behavior which the glycoprotein can be expected to exhibit in vivo, N possesses the particular advantage that N according to equation 1 covers both the clearance to be expected by way of the asialo receptor and the clearance to be expected by way of the high-Man receptor, thereby enabling more accurate predictions to be made about the clearance behavior to be expected than those provided by any of the other analytical methods mentioned.

EXAMPLE 6

N and the Storage Stability of rhu IL-4R (CHO)

In order to determine the storability of IL-4R in the fermenter harvest medium, aliquots of the harvests were stored at various temperatures (RT, +4° C., −20° C. and −70° C.). Aliquots were removed at time 0 and after 1, 2 and 3 months. The IL-4R was purified from these aliquots, in a manner known per se, by means of affinity chromatography on an immobilized anti-IL-4R monoclonal antibody. The neuraminic acid content and the N value (in analogy with Example 1) of each of the purified IL-4R samples were then determined. The results are summarized in FIG. 4.

As FIG. 4a shows, while N was found to be constant in the case of the samples stored at −70° C. and −20° C., it fell markedly, in the case of the samples stored at +4° C., and massively, in the case of those stored at RT, as the period of storage increased.

The results of the neuraminic acid determination (FIG. 4b) are of considerably less predictive value although they provide evidence of a tendency with is analogous to that of the charge number. It is consequently obvious that, from an analytical point of view, determination of the charge number is superior to neuraminic acid determination. The advantage is based on the high accuracy with which the charge number can be determined—with the particular advantage that reference to the (glyco)protein concentration is not required for determining the charge number, in contrast to determining neuraminic acid, and the inaccuracy of determining the protein is consequently not included in the test result.

Thus, it was possible to demonstrate that N is outstandingly suitable for use as a parameter for monitoring the storage stability of a glycoprotein.

EXAMPLE 7

Determining the N of rhu EPO (BHK)

The N-glycans were liberated from rhu EPO (BHK) (Merckle AG) with PNGase F in a manner known per se (Nimtz et al., *Eur. J. Biochem.* (1993) 213, 39–56).

The N value was determined, in analogy with Example 1, to be N=323 (Table 4).

Note

Nimtz et al. (*Eur. J. Biochem.* (1993) 213, 39–56) investigated the glycosylation of rhu EPO (BHK) (Merckle AG) very comprehensively in a detailed analytical study (using GC-MS, FAB-MS and $^1$H NMR). This study demonstrated that the N-glycan pool of the said rhu EPO (BHK) comprises 40.9% tetrasialylated N-glycans, 35.0% trisialylated N-glycans and 21.1% disialylated N-glycans. These data give an N value of N=40.9×4+35.0×3+21.1×2=311 for the N-glycan pool using equation 1. Surprisingly, this charge number of N=311, which was calculated using the data provided by Nimtz et al., is in very good agreement with the charge number of N=323 which was calculated as described in Example 1. The difference in the two charge numbers is 12, corresponding to a percentage difference of less than 4%. However, determining the charge number as described in Example 1 turns out to be very much cheaper, faster and simpler in comparison. Consequently, N proves to be a novel and very helpful and advantageous measurement parameter for characterizing the glycosylation status of a glycoprotein.

EXAMPLE 8

Determining the N Value of rhu EPO (CHO)

The N-glycans were liberated from rhu EPO (CHO) (Boehringer Mannheim) with PNGase F in a manner known per se (Nimtz et al., ibid.).

The N was determined, in analogy to Example 1, to be N=361 (Table 4).

Note

Watson et al. (*Glycobiology* (1994) 4, 227–237) also investigated the glycosylation of rhu EPO (CHO) (Amgen) in a detailed analytical study. This study showed that the N-glycans of the said rhu EPO (CHO) are more than 90% sialylated, a fact which explains the increase in the charge number as compared with the BHK-EPO in Example 9.

Watson et al. (ibid.) separated the N-glycan pool which was obtained after PNGase F digestion on a Waters glycopak™ DEAE-anion exchange column. Within the context of the present invention, the chromatogram depicted in FIG. 1 of the Watson et al. publication (p. 228) was used for determining the N value in accordance with equation 1.

This gave an N value for the Amgen CHO EPO of 367, which is in very good agreement with the charge number of N=361 which was determined for the Boehringer Mannheim CHO EPO in Example 8.

C. H. Hooke's doctoral thesis (Hokke et al. (1993), in Hokke, C. H. "Structure determination of glycoprotein glycans" (doctoral thesis), pp. 51–90) describes the detailed elucidation of the sugar structures of Organon Technika rhu EPO (CHO). In this connection, the thesis demonstrated that 18–20% of the N-glycans of this EPO lack one neuraminic acid residue while 3% of the N-glycans lack two neuraminic acid residues. Within the context of the present invention, the data provided by Hokke were used to determine N to be N=286. This charge number is much lower than the N of the Amgen CHO-EPO (N=367) and the N of the Boehringer Mannheim CHO-EPO (N=361), and also much lower than the N of the Merckle BHK-EPO (N=323). For this reason, it may be assumed that the clearance of the Organon Teknika CHO-EPO is substantially higher and, in association with this, that its biological activity is substantially lower.

Note

As explained in the above examples and in the introductory text, the glycosylation (and consequently the charge number) can fluctuate from batch to batch depending on the manner in which the corresponding glycoprotein is isolated. Further evidence for this is provided in Examples 9 and 10.

EXAMPLE 9

N and the Comparison of Various N-glycan Pools from AGP

Hermentin et al. (*Anal. Biochem.* (1992) 206, 419–429) compared N-glycan pools which were prepared in a variety of ways from AGP (batch 281184, Behringwerke AG) and compared these pools with an N-glycan library of AGP (LB-001, OGS) which was obtained commercially. The HPAE-PAD mapping chromatograms which were obtained in each case were published (Hermentin et al., ibid.). The said publication demonstrated that the mapping chromatograms differ due to the loss of bound N-acetylneuraminic acid—and this was documented by laying the mapping chromatograms one on top of the other (Hermentin et al., ibid., FIG. 5).

Within the context of the present invention, the charge number for each of the AGP mapping chromatograms published by Hermentin et al. (ibid., FIG. 5) was determined retrospectively (in analogy with Example 1). This indicated that the charge number increases as follows:

| Run a: | N = 248 | (LB-001, OGS; "hydrazinolysis-derived") |
| --- | --- | --- |
| Run b: | N = 262 | ("large-scale hydrazinolysis", 50 mg AGP) |
| Run c: | N = 276 | ("large-scale hydrazinolysis", 1000 mg AGP) |
| Run d: | N = 285 | ("automated hydrazinolysis", 2 mg AGP) |
| Run e: | N = 289 | ("PNGase F-derived after previous tryptic AGP digest"). |

The individual N values of the runs provide evidence in support of the differing compositions of the glycan pools. However, they also provide evidence in support of the finding, which was made by Hermentin et al. (ibid.) on the basis of comparing the mapping chromatograms, that the chromatograms for runs d and e are similar. This in turn provides evidence in support of the predictive, helpful and consequently advantageous importance of the charge number N.

EXAMPLE 10

N and the Digestion of AGP with PNGase F

Note

It is known that the N-glycans of AGP can only be cleaved off incompletely by PNGase F unless the AGP has been previously subjected to tryptic digestion and/or special detergents have been added (Nuck et al. (1990), *Glycoconjugate J.* 7, 279–286). Example 10 shows that the fact that the N-glycan pool of AGP has been incompletely isolated (when PNGase F has been used) can be demonstrated by calculating the charge number (in analogy to Example 1):

For this, the AGP N-glycans (as described in Examples 7 and 8) were isolated after a 48-hour incubation with PNGase F. The charge number of the isolated N-glycan pool was determined, in analogy to Example 1, to be N=248. This value is substantially less than the value of N=289(Run e) which was determined in accordance with Example 9. On the basis of the charge numbers, therefore, it can be concluded that the more highly charged N-glycans are evidently particularly difficult to cleave off when AGP is incubated with PNGase F as is described in Example 10 (that is without the prior digestion of AGP with trypsin as used in Example 9).

This once again provides evidence in support of the predictive and helpful, and consequently advantageous, importance of the charge number N and of its importance as a diagnostic parameter for the glycosylation status of a glycoprotein. For example, it is possible to draw conclusions about the severity of an inflammation by determining the N of AGP derived from individual donors (De Graf et al., *J. Exp. Med.* (1993), 177, 657–666).

EXAMPLE 11

N Value of Various Glycoproteins

Because N proves to be a novel and very helpful and advantageous measurement parameter for characterizing the glycosylation status of a glycoprotein, the charge numbers of various glycoproteins, which charge numbers were determined in analogy with Example 1, are listed in Table 4 by way of example. The origin of the particular glycoprotein, and the preparation or origin of the particular N-glycan pool (preparation by means of hydrazinolysis or using PNGase F, or obtained commercially from Oxford GlycoSystems (OGS), Abingdon, England) are also given in Table 4.

Consequently, N is suitable, in a very advantageous manner, for characterizing the glycosylation status of a glycoprotein.

TABLE 4

| Glycoprotein | Origin of the glycoprotein | Origin of the glycan pool | N |
|---|---|---|---|
| rhu EPO (CHO) | Boehringer Mannheim | PNGase F | 361 |
| rhu EPO (BHK) | Merckle | PNGase F | 323 |
| fetal calf serum fetuin | Sigma | "large scale" hydrazinolysis | 256 |
| Bovine fetuin | Sigma | GlycoPrep | 290 |
| Bovine pancreatic ribonuclease B | | Oxford GlycoSystems (OGS) | 15 |
| Chicken ovomucoid | | OGS | 15 |
| Porcine thyroglobulin | | OGS | 82 |
| Human alpha-1-acid glycoprotein | BW AG (Behringwerke AG) | GlycoPrep | 289 |
| Human serum transferrin | | OGS | 207 |
| Human antithrombin III | BW AG | GlycoPrep | 180 |
| Human fibrinogen | | OGS | 184 |
| Alpha-1-T-glycoprotein | BW AG | GlycoPrep | 187 |
| Alpha-1-antitrypsin | BW AG | GlycoPrep | 190 |
| Alpha-1-antichymotrypsin | BW AG | GlycoPrep | 236 |
| β-2-glycoprotein I | BW AG | GlycoPrep | 185 |
| TB6 glycoprotein | BW AG | GlycoPrep | 208 |
| Alpha-1-B-glycoprotein | BW AG | GlycoPrep | 194 |
| Alpha-2-HS glycoprotein | BW AG | GlycoPrep | 158 |
| 8S-alpha-3-glycoprotein | BW AG | GlycoPrep | 145 |
| Haptoglobulin | BW AG | GlycoPrep | 197 |

What is claimed is:

1. A process for calculating a charge number (N) for a glycoprotein, having glycans, which comprises:
   (a) isolating said glycans from said glycoprotein;
   (b) obtaining a chromatogram, having a plot over time, by performing ion exchange chromatography on said glycans, wherein asialylated N-glycans are separated in an asialo time range, monosialylated N-glycans are separated in a monosialo time range, disialylated N-glycans are separated in a disialo time range; trisialylated N-glycans are separated in a trisialo time range; tetrasialylated N-glycans are separated in a tetrasialo time range; and pentasialylated N-glycans are separated in an pentasialo time range;
   (c) setting $A_{(as)}$ equal to the area under said plot for the asialo time range, divided by the glycan area, wherein said glycan area comprises the total area under said plot from the beginning of the asialo time range to the end of the pentasialo time range;
   (d) setting $A_{(MS)}$ equal to the area under said plot for the monosialo time range divided by the glycan area;
   (e) setting $A_{(DiS)}$ equal to the area under said plot for the disialo time range divided by the glycan area;
   (f) setting $A_{(TriS)}$ equal to the area under said plot for the trisialo time range divided by the glycan area;
   (g) setting $A_{(TetraS)}$ equal to the area under said plot for the tetrasialo time range divided by the glycan area;
   (h) setting $A_{(PentaS)}$ equal to the area under said plot for the pentasialo time range divided by the glycan area; and
   (i) calculating N as equal to $A_{(as)}*0+A_{(MS)}*1+A_{(DiS)}*2+A_{(TriS)}*3+A_{(TetraS)}*4+A_{(Pentas)}*5$.

2. A process for determining the batch consistency of a batch of glycoprotein, comprising:
   (a) calculating a charge number for said batch of glycoprotein using the process of claim 1;
   (b) calculating a standard charge number for a standard glycoprotein preparation using the process of claim 1;
   (c) determining the batch consistency of said batch of glycoprotein by comparing a mathematical function of the charge number for said batch of glycoprotein with the same mathematical function of said standard charge number.

3. The process of claim 2, wherein said batch of glycoprotein has been produced by means of cell technology.

4. A process for determining the batch consistency of a batch of glycoprotein, comprising:
   (a) calculating a charge number for said batch of glycoprotein using the process of claim 1;
   (b) calculating a standard charge number N for a standard glycoprotein preparation by the process of:
      (i) setting $A_{(as)}$ equal to the percentage of asialylated N-glycans of said standard glycoprotein, as determined using GC-MS, FAB-MS and $^1$H NMR;
      (ii) setting $A_{(MS)}$ equal to the percentage of monosialylated N-glycans of said standard glycoprotein, as determined using GC-MS, FAB-MS and $^1$H NMR;
      (iii) setting $A_{(DiS)}$ equal to the percentage of disialylated N-glycans of said standard glycoprotein, as determined using GC-MS, FAB-MS and $^1$H NMR;
      (iv) setting $A_{(TriS)}$ equal to the percentage of trisialylated N-glycans of said standard glycoprotein, as determined using GC-MS, FAB-MS and $^1$H NMR;
      (v) setting $A_{(TetraS)}$ equal to the percentage of tetrasialylated N-glycans of said standard glycoprotein, as determined using GC-MS, FAB-MS and $^1$H NMR;
      (vi) setting $A_{(PentaS)}$ equal to the percentage of pentasialylated N-glycans of said standard glycoprotein, as determined using GC-MS, FAB-MS and $^1$H NMR;
      (vii) calculating the standard charge number N as equal to $A_{(as)}*0+A_{(MS)}*1+A_{(DiS)}*2+A_{(TriS)}*3+A_{(TetraS)}*4+A_{(PentaS)}*5$; and
   (c) determining the batch consistency of said batch of glycoprotein by comparing the charge number for said batch of glycoprotein with said standard charge number.

5. The process of claim 4, wherein said batch of glycoprotein has been produced by means of cell technology.

6. The process of claim 1, wherein said glycans are isolated from said glycoprotein by means of hydrazinolysis.

7. The process of claim 1, wherein said glycans are isolated from said glycoprotein using an enzyme.

8. The process of claim 7, wherein said enzyme is PNGaseF.

9. The process of claim 1, wherein the ion exchange chromatography is high-PH anion exchange chromatography with pulsed amperometric detection (HPAE-PAD).

10. The process as claimed in claim 1 for checking the disease status of a species based on the charge number N of a glycoprotein which is characteristic for the disease.

11. The process as claimed in claim 1 for checking the disease status of a patient based on the charge number N of a glycoprotein which is characteristic for the disease.

12. A process for determining the batch consistency of a batch of glycoprotein, comprising:
   (a) calculating a charge number for said batch of glycoprotein using the process of claim 1;
   (b) calculating a first value based on said charge number;
   (c) calculating a standard charge number for a standard glycoprotein preparation using the process of claim 1;

(d) calculating a second value based on said standard charge number;

(e) determining the batch consistency of said batch of glycoprotein by comparing said first value with said second value.

13. A process for determining the batch consistency of a batch of glycoprotein, comprising:

(a) calculating a charge number for said batch of glycoprotein using the process of claim 1;

(b) calculating a first value based on said charge number;

(c) calculating a standard charge number N for a standard glycoprotein preparation by the process of:

(i) setting $A_{(as)}$ equal to the percentage of asialylated N-glycans of said standard glycoprotein, as determined using GC-MS, FAB-MS and $^1$N NMR;

(ii) setting $A_{(MS)}$ equal to the percentage of monosialylated N-glycans of said standard glycoprotein, as determined using GC-MS, FAB-MS and $^1$N NMR;

(iii) setting $A_{(DiS)}$ equal to the percentage of disialylated N-glycans of said standard glycoprotein, as determined using GC-MS, FAB-MS and $^1$N NMR;

(iv) setting $A_{(TriS)}$ equal to the percentage of trisialylated N-glycans of said standard glycoprotein, as determined using GC-MS, FAB-MS and $^1$N NMR;

(v) setting $A_{(TetraS)}$ equal to the percentage of tetrasialylated N-glycans of said standard glycoprotein, as determined using GC-MS, FAB-MS and $^1$N NMR;

(vi) setting $A_{(PentaS)}$ equal to the percentage of pentasialylated N-glycans of said standard glycoprotein, as determined using GC-MS, FAB-MS and $^1$N NMR;

(vii) calculating the standard charge number N as equal to $A_{(as)}*0+A_{(MS)}*1+A_{(DiS)}*2+A_{(TriS)}*3+A_{(TetraS)}*4+A_{(PentaS)}*5$;

(d) calculating a second value based on said standard charge number; and (e) determining the batch consistency of said batch of glycoprotein by comparing said first value with said second value.

14. A process for calculating a charge number (N) for a glycoprotein, having glycans, which comprises:

(a) measuring the percentage of asialo N-glycans, monosialo N-glycans, disialo N-glycans, trisialo N-glycans, tetrasialo N-glycans and pentasialo N-glycans of said glycoprotein using GC-MS, FAB-MS, and $^1$H NMR;

(b) setting $A_{(as)}$ equal to the percentage of asialylated N-glycans of said glycoprotein;

(c) setting $A_{(MS)}$ equal to the percentage of monosialylated N-glycans of said glycoprotein;

(d) setting $A_{(DiS)}$ equal to the percentage of disialylated N-glycans of said glycoprotein;

(e) setting $A_{(TriS)}$ equal to the percentage of trisialylated N-glycans of said glycoprotein;

(f) setting $A_{(TetraS)}$ equal to the percentage of tetrasialylated N-glycans of said glycoprotein;

(g) setting $A_{(PentaS)}$ equal to the percentage of pentasialylated N-glycans of said glycoprotein; and (h) calculating N as equal to $A_{(as)}*0+A_{(MS)}*1+A_{(DiS)}*2+A_{(TriS)}*3+A_{(TetraS)}*4+A_{(PentaS)}*5$.

15. A process for the in vivo determination of the bioavailability of a glycoprotein, comprising:

(a) calculating a charge number (N) for said glycoprotein using the process of claim 1;

(b) establishing a mathematical relationship between bioavailability and charge number (N), using a database of glycoproteins having a certain calculated (N) and having a certain bioavailabilty determined by in vivo testing, wherein N is calculated by using the method of claim 1 or claim 14, and (c) calculating the bioavailabilty if said glycoprotein using said mathematical relationship.

* * * * *

UNITED STATES PATENT AND TRADEMARK OFFICE
CERTIFICATE OF CORRECTION

PATENT NO.   : 6,096,555
DATED        : August 1, 2000
INVENTOR(S)  : Peter Hermentin et al.

It is certified that error appears in the above-identified patent and that said Letters Patent is hereby corrected as shown below:

Column 15,
Line 46, "an pentasialo" should read -- a pentasialo --.
Line 65, "*4+$A_{(Pentas)}$" should read -- *4+$A_{(PentaS)}$ --.

Column 18,
Line 24, "in vivo" should read -- in vitro --.
Line 34, "if said" should read -- of said --.

Signed and Sealed this

Eighth Day of October, 2002

Attest:

JAMES E. ROGAN
Attesting Officer          Director of the United States Patent and Trademark Office